(12) United States Patent
Wang et al.

(10) Patent No.: US 12,295,650 B2
(45) Date of Patent: May 13, 2025

(54) DEVICE FOR MAPPING AND ABLATING RENAL NERVES DISTRIBUTED ON THE RENAL ARTERY

(71) Applicant: SYMAP MEDICAL (SUZHOU), LTD, Jiangsu (CN)

(72) Inventors: Jie Wang, Englewood Cliffs, NJ (US); Chuwu Li, Chengdu (CN); Bo Zou, Sichuan (CN); Jiancong Wang, Sichuan (CN)

(73) Assignee: SYMAP MEDICAL (SUZHOU), LTD, Suzhou (CN)

( * ) Notice: Subject to any disclaimer, the term of this patent is extended or adjusted under 35 U.S.C. 154(b) by 0 days.

(21) Appl. No.: 17/750,422

(22) Filed: May 23, 2022

(65) Prior Publication Data

US 2022/0287770 A1    Sep. 15, 2022

Related U.S. Application Data

(63) Continuation of application No. 15/691,768, filed on Aug. 31, 2017, now Pat. No. 11,337,748, which is a
(Continued)

(30) Foreign Application Priority Data

Mar. 6, 2013    (CN) .......................... 201310070820.3

(51) Int. Cl.
*A61B 18/14*    (2006.01)
*A61B 5/00*    (2006.01)
(Continued)

(52) U.S. Cl.
CPC ........ *A61B 18/1492* (2013.01); *A61B 5/0205* (2013.01); *A61B 5/201* (2013.01);
(Continued)

(58) Field of Classification Search
CPC ................ A61B 5/201; A61B 18/1492; A61B 2018/00202; A61B 2018/00404;
(Continued)

(56) References Cited

U.S. PATENT DOCUMENTS 6,171,275 B1 *    1/2001    Webster, Jr. ....... A61B 18/1492
                                                                        604/20
9,770,291 B2 *    9/2017    Wang ................... A61B 5/4833
(Continued)

*Primary Examiner* — Michael F Peffley
*Assistant Examiner* — Samantha M Good
(74) *Attorney, Agent, or Firm* — Law Offices of Albert Wai-Kit Chan, PLLC

(57) ABSTRACT

This invention relates to a device for mapping and ablating the renal nerves distributed on the renal artery, said device comprising a guide catheter, a mapping-ablation catheter, a handle and a connector. The guide catheter has at least one lumen and a distal end with adjustable curvature. The mapping-ablation catheter is housed in one of the lumens of the guide catheter and its distal end has one or more electrodes and one or more detecting devices. The distal end of the mapping-ablation catheter is curved, rotatable, and can be extended out of or retracted into the guide catheter. The handle connects the guide catheter and mapping-ablation catheter, and comprises one or more controlling components for controlling the movement of the guide catheter and mapping-ablation catheter. The connector is designed to supply energy to the electrodes.

18 Claims, 7 Drawing Sheets

Related U.S. Application Data continuation of application No. 14/421,869, filed as application No. PCT/CN2013/082135 on Aug. 23, 2013, now Pat. No. 9,770,291, which is a continuation-in-part of application No. PCT/IB2012/054310, filed on Aug. 24, 2012.

(60) Provisional application No. 61/693,019, filed on Aug. 24, 2012, provisional application No. 61/609,565, filed on Mar. 12, 2012, provisional application No. 61/527,893, filed on Aug. 26, 2011.

(51) Int. Cl.
| | | |
|---|---|---|
| *A61B 5/0205* | (2006.01) | |
| *A61B 5/20* | (2006.01) | |
| *A61B 5/24* | (2021.01) | |
| *A61B 18/00* | (2006.01) | |
| *A61B 5/024* | (2006.01) | |
| *A61N 1/36* | (2006.01) | |

(52) U.S. Cl.
CPC ............ *A61B 5/24* (2021.01); *A61B 5/4893* (2013.01); *A61B 5/6852* (2013.01); *A61B 5/024* (2013.01); *A61B 2018/00202* (2013.01); *A61B 2018/00404* (2013.01); *A61B 2018/00434* (2013.01); *A61B 2018/00505* (2013.01); *A61B 2018/00511* (2013.01); *A61B 2018/00577* (2013.01); *A61B 2018/00642* (2013.01); *A61B 2018/00791* (2013.01); *A61B 2018/00839* (2013.01); *A61B 2018/00875* (2013.01); *A61B 2018/1475* (2013.01); *A61N 1/36117* (2013.01)

(58) Field of Classification Search
CPC .......... A61B 2018/00434; A61B 2018/00505; A61B 2018/00511; A61B 2018/1475
See application file for complete search history.

(56) References Cited

U.S. PATENT DOCUMENTS

| | | | | |
|---|---|---|---|---|
| 11,337,748 | B2 * | 5/2022 | Wang | .................. A61B 5/0205 |
| 2002/0082594 | A1 * | 6/2002 | Hata | .................. A61B 18/1492 |
| | | | | 606/41 |
| 2011/0264011 | A1 * | 10/2011 | Wu | ....................... A61F 5/0013 |
| | | | | 601/2 |

* cited by examiner

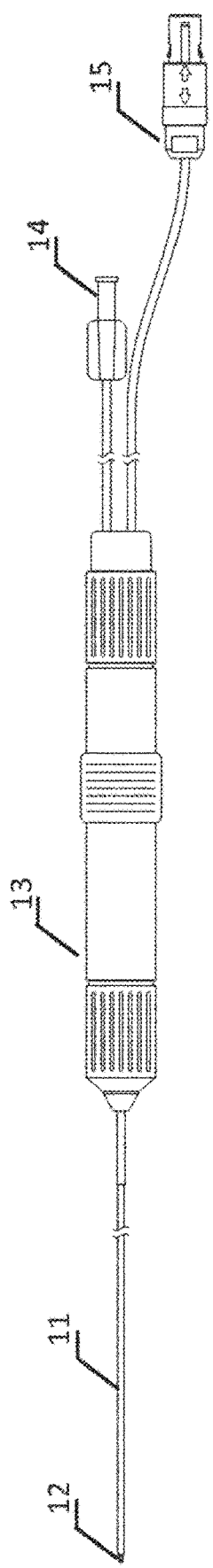
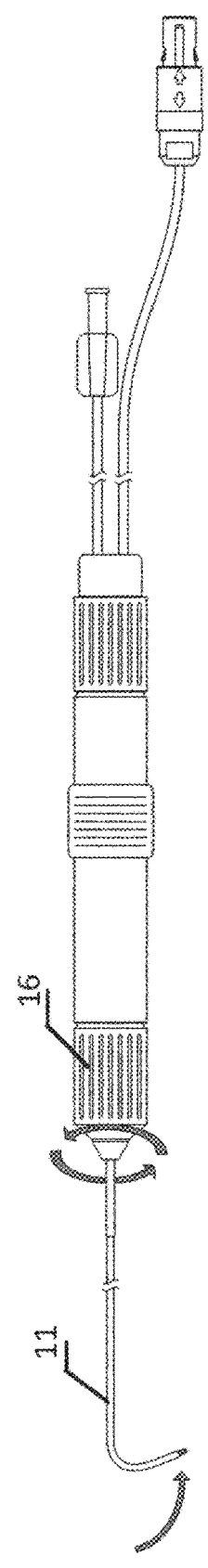
Fig. 1-1
Fig. 1-2

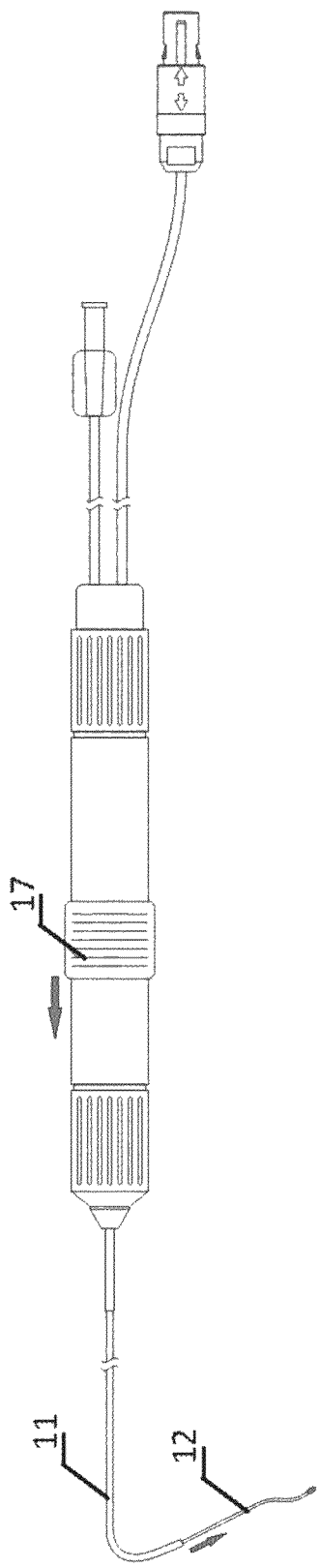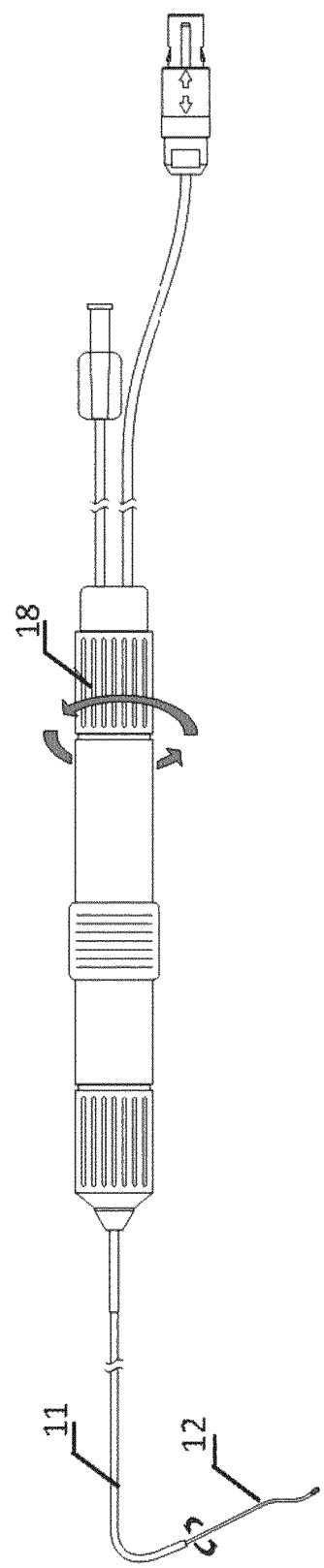
Fig. 1-3
Fig. 1-4

DEVICE FOR MAPPING AND ABLATING RENAL NERVES DISTRIBUTED ON THE RENAL ARTERY

This application is a continuation application of U.S. Ser. No. 15/691,768, filed Aug. 31, 2017 (now U.S. Pat. No. 11,337,748) which is a continuation application of U.S. Ser. No. 14/421,869, filed Feb. 16, 2015 (now U.S. Pat. No. 9,770,291) which claims priority to the international application PCT/IB2012/054303 filed on Aug. 24, 2012, the international application PCT/IB2012/054310 filed on Aug. 24, 2012, U.S. 61/693,019 filed on Aug. 24, 2012 and Chinese application 201310070820.3 filed Mar. 6, 2013. The contents of the preceding applications are hereby incorporated in their entireties by reference into this application. Throughout this application, various publications are referenced. Disclosures of these publications in their entireties are hereby incorporated by reference into this application in order to more fully describe the state of the art to which this invention pertains.

FIELD OF THE INVENTION

This invention relates to a catheter device system for mapping and ablating renal nerves distributed on renal artery so as to improve the accuracy, effectiveness and safety of catheter-based renal nerve ablation.

BACKGROUND OF THE INVENTION

Hyperactivity of renal sympathetic nerve is a pathophysiological mechanism in diseases such as congestive heart failure (CHF), hypertension, diabetes, chronic renal failure, arrhythmia and other heart disorder. The renal sympathetic denervation method has been applied recently to treat these diseases because this therapy method can reduce the hyperactivity of sympathetic nerve. In general, all diseases with hyperactivity of sympathetic nerve as one of its pathological mechanisms can be treated with the renal sympathetic denervation approach. The renal sympathetic nerve is believed to be both an effector and sensor of the sympathetic system, thus the pathophysiological status of the cardiovascular system and other organs can be regulated via the renal sympathetic nerve.

Possible Clinical Applications of Renal Sympathetic Denervation Procedure

1. Hypertension: Krum et al studied the effects of catheter-based renal sympathetic denervation on blood pressure in patients with hypertension. Two studies have been completed and published: Symplicity HTN-1 (Krum et al., 2009; Sadowski et al., 2011) and Symplicity HTN-2 (Esler et al., 2010). One study is under way: Symplicity HTN-3. Symplicity HTN-1 and Symplicity HTN-2 included 50 and 106 patients, with the follow-up periods of 12 and 6 months, respectively. No detail has been reported for Symplicity HTN-3 to date. All studied subjects in these studies were patients with drug resistance hypertension, i.e. their systolic pressure was still ≥160 mmHg after administration of at least three types of anti-hypertensive drugs including a diuretic, or those patients for whom it is impossible to treat their hypertension with drug therapies due to various reasons. In Symplicity HTN-1, in 45 patients who had received renal denervation procedure, their average systolic/diastolic blood pressure dropped from 177/101 mmHg by −14/−10, −21/−10, −22/−11, −24/−11 and −27/17 mmHg at 1, 3, 6, 9 and 12 months respectively after the treatment. The blood pressure level in 5 patients who did not receive this treatment was increased during the same time period (Krum et al., 2009). In Symplicity HTN-2 study, which was a randomized study having a control group, ambulatory blood pressure monitoring replaced manual blood pressure measurement in the outpatient office in order to avoid the "white coat effect", and the effects of renal denervation on hypertension further confirmed the results in Symplicity HTN-1. At 1, 3 and 6 months after the procedure, systolic and diastolic blood pressure in 52 patients also dropped by 20/−7, −24/−8 and −32/−12 mmHg respectively from their hypertensive baseline (Esler et al., 2010). The average time spent on the renal denervation procedure was only about 38 minutes, low radio frequency energy was used (5~8 W), the spacing between ablation points was at least 5 mm apart, with 4~6 ablation points on each side of renal artery, and the ablation time for each point was 2 min (Sobotka et al., 2012). This method was safe, and up to now, no side effects such as vascular thrombosis, renal embolism or renal function impairment were reported.

2. Abnormal glucose metabolism and diabetes: Mahfoud et al studied 37 patients with various clinical syndromes of diabetes 3 months after the renal sympathetic denervation procedure. It was found that the fasting level of blood glucose dropped from 118 to 108 mg/dL, insulin level dropped from 20.8 to 9.3 μIU/mL, C-peptide level reduced from 5.3 to 3.0 ng/mL, while insulin resistance reduced from 6.0 to 2.4, and the glucose level 2 hours after oral glucose tolerance test also reduced by 27 mg/dL. In the control group, the blood pressure and the levels of these metabolism markers in 13 patients who did not receive renal denervation procedure were not significant changed (Mahfoud et al., 2011). The results demonstrated that renal denervation can improve the insulin resistance and glucose metabolism in patients with diabetes.

3. Sleep apnea syndrome (SAS): Witkowski et al found that renal sympathetic denervation procedure can significantly improve sleep apnea in patients with drug resistant hypertension. They found that, 6 months after renal denervation, apnea hypopnea index (AHI) in 10 patients with drug resistance hypertension accompanied with sleep apnea reduced from 16.3 times/h (before the procedure) to 4.5 times/h. These results indicate that, in patients with both drug resistant hypertension and sleep apnea, this treatment method can improve the degree of sleep apnea while reducing the blood pressure of patients (Witkowski et al., 2011).

4. Heart failure: Brandt et al reported that 6 months after renal sympathetic denervation procedure in patients with drug resistance hypertension, the left ventricle hypertrophy index, left ventricular septum thickness, left ventricular end diastolic volume, isovolumetric relaxing period and left ventricular filling pressure were significantly reduced, while the cardiac ejection fraction was increased significantly. Similar changes of these parameters were not observed in 18 patients who were served as control group and did not receive this treatment (Brandt et al., 2012). These results indicate that renal sympathetic denervation procedure can significantly improve cardiac functions of patients with cardiac dysfunction. Symplicity-H and REACH are ongoing clinical studies investigating the impacts of renal sympathetic denervation procedure on patients with heart failure, but no results have yet been published (Sobotka et al., 2012).

5. Chronic kidney diseases and renal failure: hyperactivity and excessive tone of sympathetic nerve are closely related to the occurrence and development of chronic renal failure. Factors which impair the kidneys can cause hyperactivity of systemic sympathetic nerve via the renal nerve; the pathological high systemic sympathetic tone is harmful to kidney, directly resulting in impairment of renal function (Schlaich et al., 2009). Therefore, reducing the hyperactivity of systemic sympathetic nerve by renal sympathetic denervation procedure may also be a new means to treat chronic kidney diseases and renal failure. It has been reported that one year after the renal sympathetic denervation procedure, patients with late stage chronic kidney disease and drug resistance hypertension showed no significant change in eGFR (Hering et al., 2012; Hering et al., 2012; Dasgupta et al., 2012). The result indicates that the treatment can probably slow down the progress of chronic kidney disease.

6. High sympathetic tone related-cardiovascular diseases: it has been shown in animal and clinical studies that high sympathetic tone plays an important role in the occurrence and development of many cardiovascular diseases (D'Agrosa, 1997; Esler, 1992). Thus, renal sympathetic denervation which can rebalance the high systemic sympathetic tone by suppressing the hyperactivity of systemic sympathetic nerve may be used in treatment of cardiovascular diseases such as arrhythmia and heart failure.

However, in the existing procedures for renal nerve ablation or other renal denervation methods, the distribution of renal nerves is not located, and the surgeon does not know on which part of the renal artery should the renal denervation procedure be performed. Therefore the operation is performed blindly, and its treatment effect and safety should be further improved and raised. In particular, Brinkmann et al recently did ablation procedure to remove renal nerves in 12 patients with hypertension, but blood pressure was only reduced in 3 patients after the treatment, and the blood pressure did not reduce in other 7 patients after the treatment (Brinkmann et al., 2012). Somehow, these investigators did report changes in blood pressure in the rest of 2 patients in their publication. These investigators believed that one of the reasons was that the renal nerve ablation procedure was not made at the distribution point of the renal sympathetic nerve. Brinkmann et al. also expressed that it was not known whether the radio frequency energy applied in the procedure ablated the renal afferent or efferent nerves. Essentially, surgeons have no clinical indicator to assess and prove if the procedure is successfully performed (Brinkmann et al., 2012). Therefore, there is an urgent need clinically for a practical and feasible method to map the renal sympathetic nerve and the renal parasympathetic nerve, to direct clinical doctors how to remove renal sympathetic nerves in an accurate, effective and safe manner, and to assess and prove if the renal denervation operation is successfully performed.

The US patent application, US 2011/0306851 A1, puts forth a specific method for renal sympathetic nerve mapping and devices to implement renal sympathetic nerve mapping for the first time. In the patent specification, pig experiments were performed to demonstrate how to map the distribution of renal sympathetic nerves by applying electric stimulation within renal artery while monitoring changes in artery blood pressure, heart rate and other physiological parameters. If a given position of the renal artery is stimulated and blood pressure and heart rate were increased, that position is determined as a distributed point by renal sympathetic nerve. This renal sympathetic mapping concept and approaches were recently confirmed by other investigators. Using dog model, Chinushi et al. (Chinushi et al., 2013) reported that once intra-renal electronic simulation was applied to certain locations of renal artery, blood pressure and heart rate were increased. After these locations were ablated using high radio frequency and the same electric stimulation was applied to the same location again, blood pressure and heart rate no longer changed.

Renal sympathetic denervation provides an alternative therapy to treat diseases which are related to hyperactivity of sympathetic nerve system, thus there is a clinical need to have devices with functions to perform intra-renal artery stimulation and renal denervation. Devices used for the two above-mentioned studies were not specially designed for renal nerve mapping and ablation. The current catheter and ablation systems which have been used by clinicians were designed for cardiac ablation and cardiac diseases such as arrhythmia with very high energy. The configuration and shape of these catheters were not designed according to renal artery anatomy and structure but were rather based on coronary artery/cardiac anatomy and structure. These catheter systems have electrodes at their tips which were designed to detect abnormal electric physiology in cardiac tissues; however, these designs did not meet the needs of physicians for mapping and ablating renal sympathetic and parasympathetic nerves. An ideal renal nerve mapping and ablation catheter system should have dual functions: it should deliver electrical stimulations from within the renal artery to map the distributions of renal sympathetic and parasympathetic nerves, and also deliver energy to ablate renal nerves. At the same time, the shape of the catheter should be optimized for the anatomical structure of renal artery. Using such a catheter system, physicians will be able to deliver intra-renal stimulation, monitor physiological changes in patient during the stimulation, ablate renal sympathetic innervations, and stimulate these positions again to evaluate whether a successful renal sympathetic denervation has been performed. However, up to date, a catheter system to meet these requirements has not yet been developed.

During renal denervation procedure, the anatomy and structure of the renal artery must be taken into consideration. The variations of the renal artery among individuals are very large such as differences in length, diameter and bifurcations. Patients with hypertension may have implanted renal stents, renal artery stenosis, renal artery plaques or other anatomy abnormalities. If these factors were not taken into consideration, for some existing ablation catheter systems with ablation energy that is too high (renal artery ablation is low energy procedure and it cannot be more than 8 watts), serious side effects may occur during the procedure such as vessel spasms, edema, renal artery endothelial denudation, embolism, rupture, necrosis and stenosis. Thus, an ablation catheter system designed according to renal artery anatomy, structure, physiology and biology with low energy, and having both functions of mapping and ablation is an urgent need for renal denervation.

In summary, current commercially available ablation catheter systems are not suitable for renal mapping and ablation since they are neither designed based on the anatomy of the renal artery nor for the purpose of mapping renal sympathetic/parasympathetic nerves. These ablation catheter systems cannot fulfill the clinical needs of renal denervation which require accuracy, efficacy and safety. This invention will address these issues.

SUMMARY OF THE INVENTION

This invention provides a catheter device system for mapping and ablating renal nerves distributed on renal arteries so as to improve the accuracy, effectiveness and safety of catheter-based renal nerve ablation procedure.

In one embodiment, the present invention provides a device for mapping and ablating the renal nerves distributed on the renal artery, comprising a guide catheter, a mapping-ablation catheter, a handle and a connector, wherein said guide catheter has at least one lumen and a distal end with adjustable curvature; said mapping-ablation catheter is housed in one of the lumens of the guide catheter and has a distal end that comprises one or more electrodes and one or more detecting devices, said distal end of the mapping-ablation catheter is curved and can be extended out of or retracted into the guide catheter and is rotatable along the central axis of the open end of the guide catheter; said handle connects the guide catheter and mapping-ablation catheter and comprises one or more controlling components, said controlling components are for controlling the movement of the guide catheter and mapping-ablation catheter; and said connector is designed to supply energy to the electrode.

In one embodiment, said handle further comprises a fluid-exchange conduit connected to the guide catheter for controlling fluid entering or leaving the guide catheter. In another embodiment, said detecting devices comprise temperature detecting device and resistance detecting device. In another embodiment, said electrodes comprise electrodes for delivering electrical energy, radio frequency energy, laser energy, high intensity focused ultrasound, or for carrying out cryoablation.

In one embodiment, a sealing mechanism is formed between the mapping-ablation catheter and guide catheter to control fluid entry or exit.

In one embodiment, the material at the distal end of said guide catheter is the softest, the material at the middle part of the guide catheter has an intermediate hardness and the material at the proximal end of the guide catheter is the hardest with the hardness of the materials distributed in the range 90 A to 80 D in the Shore hardness scale.

In one embodiment, the curvature of the distal end of said mapping-ablation catheter is maintained by using a traction wire, one end of the traction wire is fixed to the distal end of the mapping-ablation catheter while the other end is fixed to a spring inside the handle, wherein when the distal end of the mapping-ablation catheter is retracted into the guide catheter, the distal end is confined and stretches the traction wire to compress the spring, wherein when the distal end of the mapping-ablation catheter is extended out of the guide catheter, its distal end is no longer confined and the spring restores naturally and pulls the traction wire to cause the bending of the distal end of the catheter; or by using Ni—Ti shape memory alloy with a preformed shape so that the distal end can maintain the preformed curvature after assembled into the catheter.

In one embodiment, said controlling components comprise a control knob that causes the distal end of the guide catheter to bend. In one embodiment, said controlling components comprise a control knob that causes the distal end of the mapping-ablation catheter to extend out of or withdraw into the guide catheter. In another embodiment, said controlling components comprise a control knob that causes the distal end of the mapping-ablation catheter to rotate. In another embodiment, said controlling components comprise a control knob that causes the distal end of the mapping-ablation to extend out of or withdraw into the guide catheter, and causes the distal end of the mapping-ablation catheter to rotate.

The present invention also provides a method of using the device disclosed herein for mapping and ablating the renal nerves distributed on a renal artery, said method comprising the following steps: (i) inserting the distal end of the guide catheter of the device into renal artery via the abdominal aorta; (ii) extending the mapping-ablation catheter out of the guide catheter to establish good contact between the electrode and the renal artery wall; and (iii) providing energy to the electrode, so that said energy is delivered to the renal artery wall. In one embodiment, the curvature of the distal end of the guide catheter is adjustable to make it easier to enter the renal artery. In another embodiment, the length of the mapping-ablation catheter extending out of the guide catheter is controllable to allow selection of a position to establish good contact between the electrode and the renal artery wall. In another embodiment, said mapping-ablation catheter can be controlled to rotate around the central axis of the open end of the guide catheter to allow selection of a position to establish good contact between the electrode and the renal artery wall. In one embodiment, said energy to be delivered into the renal artery wall comprises energy for nerve stimulation and energy for nerve ablation. In another embodiment, said energy comprises electric energy, radio frequency energy, laser energy, high density focusing supersonic wave, or for cryoablation. In yet another embodiment, the above method further comprises the step of moving the guide catheter or mapping-ablation catheter, after step (iii), to establish good contact between the electrode and the renal artery wall at a new location.

BRIEF DESCRIPTION OF THE FIGURES

FIG. 1-1 shows one embodiment of the catheter device system of this invention. The catheter device system comprises a guide catheter (11) having two lumens wherein the curvature of the distal end is adjustable; a steerable mapping-ablation catheter (12) housed within the guide catheter (11) wherein said mapping-ablation catheter is steerable and has a distal end with a preformed shape; a handle (13) containing controlling components; a fluid-exchange conduit (14) located at the end of the handle that is connected with the guide catheter; a connector (15) at the end of the handle for connecting with the mapping and ablating controller; and traction wires connecting the distal end of the guide catheter to the controlling components. The mapping-ablation catheter is retracted into the guide catheter in the figure shown.

FIG. 1-2 shows the catheter device in FIG. 1-1 when the distal end of the guide catheter (11) was bent after the control knob (16) was rotated.

FIG. 1-3 shows the catheter device in FIG. 1-1 when the mapping-ablation catheter (12) was extended out of the guide catheter (11) after the control knob (17) was pushed.

FIG. 1-4 shows the catheter device in FIG. 1-1 when the mapping-ablation catheter (12) extending out of the guide catheter (11) rotated around the central axis of the open end of the guide catheter (11) after the control knob (18) was turned.

FIG. 2-1 shows an embodiment of the distal end (21) of the mapping-ablation catheter wherein the tip of the catheter has an electrode (22) and a temperature detecting device (23), wherein within the distal end of the catheter there is a traction wire (21) or shape memory device (25) that cause the distal end to assume a fixed curvature or adjustable curvature.

FIG. 2-2 shows an embodiment of the distal end of the mapping-ablation catheter. A sealing mechanism between the tip of the mapping-ablation catheter (12) and the guide catheter (11) is formed by the smooth surface of the electrode (22) fitting neatly on the smooth edge of the open end of the guide catheter (11). The traction wire (24) of the mapping-ablation catheter and the traction wire (26) of the guide catheter (11) are made of stainless steel or Ni—Ti alloy.

FIG. 3-1 shows another embodiment of this invention; said catheter device differs from the embodiment of FIG. 1 by having a control knob (19) that can be moved forward and backward or rotated. The mapping-ablation catheter is retracted into the guide catheter in the figure shown.

FIG. 3-2 shows an embodiment of the mechanism for controlling the bending of the guide catheter (11). The control knob (16) drives the sliding block (31) by means of a screw thread mechanism. Rotating the control knob (16) causes the sliding block (31) move linearly on the slideway (32). One end of a traction wire is fixed to the sliding block (31) while the other end is connected to the tip of the guide catheter. The distal end of the guide catheter will be bent as the traction wire is pulled.

FIG. 3-3 shows an embodiment of the mechanism for extending the mapping-ablation catheter (12) out of the guide catheter (11). The control knob (19) contacts the rotation-fixing block (34) via the structural component (33) and the rotation-fixing block (34) has a groove ring at its contact with the structural component (33) to ensure that the structural component will not rotate with the rotation-fixing block when the rotation-fixing block rotates. When the control knob (19) is pushed, the control knob (19) drives the rotation-fixing block (34) and the mapping-ablation catheter (12) fixed on it to move forward and backward via the structural component (33) so that the mapping-ablation catheter (12) can extend out of or withdraw into the guide catheter (11) by moving the control knob (19) forward and backward.

FIG. 3-4 shows an embodiment of the mechanism for rotating the mapping-ablation catheter (12) around the central axis of the open end of the guide catheter (11). The control knob (19) contacts the rotation-fixing block (34) via the gear set (35). The outside of the rotation-fixing block (34) is designed with teeth so that motion the gear set (35) could be transmitted. As the fixing block (36) fixes the mapping-ablation catheter (12) on the rotation-fixing block (34) by pressing against the proximal end of the catheter (stainless steel pipe) under the action of a screw, turning the control knob (19) will transmit the motion to the gear set (35) which then rotates the rotation-fixing block (34) such that the mapping-ablation catheter (12) will rotate around the central axis of the open end of the guide catheter (11).

DETAILED DESCRIPTION OF THE INVENTION

Figures 1, 2:
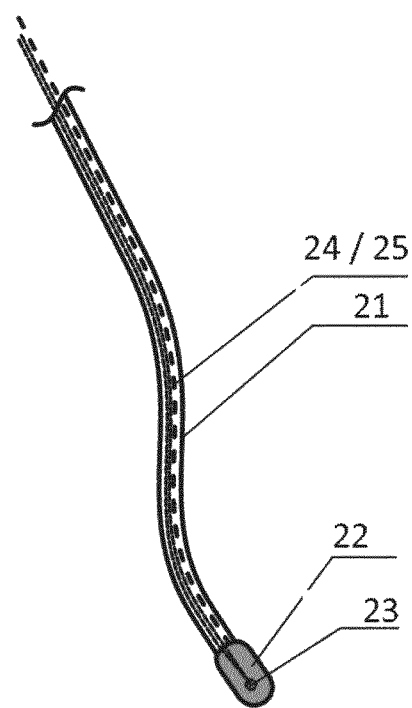
Figure 2:
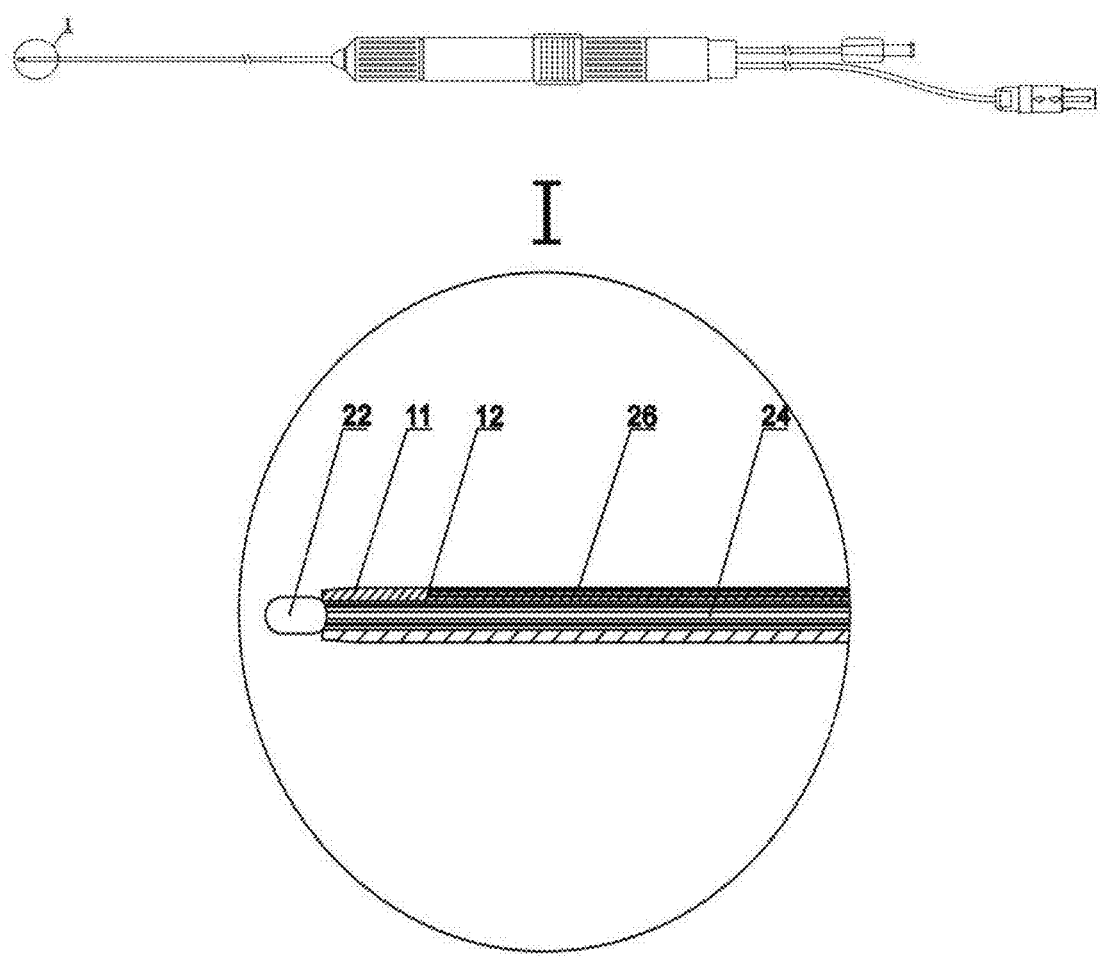

The invention will be better understood by reference to the Experimental Details which follow, but those skilled in the art will readily appreciate that the specific examples are for illustrative purposes only and should not limit the scope of the invention which is defined by the claims which follow thereafter.

In one embodiment, this invention provides a catheter device system for mapping and ablating renal nerves distributed on a renal artery, said catheter device system comprises a guide catheter having two lumens wherein the curvature of the distal end is adjustable; a mapping-ablation catheter housed within the guide catheter wherein said mapping-ablation catheter is steerable and has a distal end with a preformed shape; a handle containing controlling components; a fluid-exchange conduit located at the end of the handle that is linked to the guide catheter; a connector at the end of the handle for connecting with external instruments; and traction wires linking the distal end of the guide catheter to the controlling components.

In one embodiment, this invention provides a single catheter for carrying out multiple functions that integrates the mapping-ablation catheter and guide catheter into one device; its electrode can deliver energy for electrical stimulation or for ablation of underlying nerves in a renal artery so as to achieve the purpose of either mapping or ablation of nerves. In another embodiment, this invention allows users to inject contrast agents, collect blood samples or inject drug for treatment via the guide catheter. In yet another embodiment, the distal ends of the device of this invention is steerable to adjust to the structure of renal artery or the relative position between the abdominal aorta and the renal artery so that users have better control over the catheter. This makes it easier for the catheter to enter the renal artery and precisely select the location for which the electrode at the catheter tip contacts the renal arterial wall. The distal end of the catheter also has a structure that allows it to anchor at the selected location to ensure that the catheter tip will not be displaced during the procedure.

In one embodiment, the controlling components contained in the handle comprises one or more control knobs for controlling the mapping-ablation catheter and the distal end of the guide catheter. In another embodiment, said control knob is connected to the handle, mapping-ablation catheter and traction wires wherein said connection with the handle is fixed or allows rotation or sliding. The connection with the mapping-ablation catheter can be fixed connection or coaxial fixed connection.

In one embodiment, one or more traction wires within the guide catheter connects the tip of said catheter to one or more controlling components in the handle so that the distal end of the catheter will bend by manipulating said one or more controlling components. In another embodiment, said controlling components comprise one or more sliding blocks and control knobs wherein said control knob drives the movement of said one or more sliding blocks with a screw thread mechanism. Rotating said control knob causes the sliding block to move linearly on a slideway and, since one end of the traction wire is fixed on the sliding block, and the other end is connected to the tip of the guide catheter, the distal end of the guide catheter will be bent under the pulling of the traction wire.

In one embodiment, the mapping-ablation catheter is fixed to one or more controlling components inside the handle so that said mapping-ablation catheter can be pushed out of the guide catheter by manipulating said one or more controlling components. The length that is pushed out can also be controlled. In another embodiment, said controlling components comprise a control knob, a structural part and a rotation-fixing block. In another embodiment, said control knob contacts the rotation-fixing block via the structural part and the rotation-fixing block has a ring groove at its point of contact with the structural part to ensure that the structural part will not rotate with the rotation-fixing block when the rotation-fixing block rotates. In yet another embodiment, when the control knob is pushed, the knob drives the rotation-fixing block to move forward and backward via the structural part and, since the electrode at the catheter tip is fixed to the rotation-fixing block, said electrode will move according to the movement of the rotation-fixing block. In one embodiment, calibrated markings at the control knob on the handle allow precise control of the length of the mapping-ablation catheter that is extended out of or retract into the guide catheter, e.g. 5 mm, 10 mm, 15 mm, 20 mm, 25 mm, 30 mm, 35 mm, 40 mm, 45 mm, 50 mm, 55 mm, 60 mm, 65 mm, 70 mm, 75 mm and 80 mm, etc. Precise control of the length extended out of the guide catheter can ensure a minimum spacing between ablation points, such as 5 mm. In one embodiment, the mapping-ablation catheter extending out of the guide catheter can be retracted into the guide catheter with the same control knob or other control knobs.

In one embodiment, the mapping-ablation catheter is fixed to one or more controlling components on the handle, so that the mapping-ablation catheter is rotatable by manipulating one or more controlling components. In another embodiment, said controlling components comprise a control knob, gears or gear set, a rotation-fixing block and a fixing block. In yet another embodiment, said control knob contacts the rotation-fixing block via the gears or gear set and the outside of the rotation-fixing block is designed with teeth so that motion from the gears or gear set can be transmitted. In one embodiment, the electrode at the catheter tip is fixed with the rotation-fixing block so that said electrode will move according to the movement of the rotation-fixing block. In another embodiment, the electrode at the catheter tip is fixed by pressing the fixing block against the proximal end of the catheter (stainless steel pipe) under the action of a screw. In one embodiment, rotation of the control knob drives the gears or gear set which rotates the rotation-fixing block, and, in turn, causes the rotation of the electrode at the catheter tip. In another embodiment, calibrated markings at the control knob on the handle allow precise control of the amount by which the mapping-ablation catheter rotates, each marking represents rotation by a given angle up to 360° to ensure there is no blind spot when electrical stimulation is delivered. For example, each marking represents rotation of the mapping-ablation catheter by 15°.

In one embodiment, the movements of the control knobs occur along sideways (slide) at the point of contact with the handle. In another embodiment, the length of said slideway limits the range of forward or backward movement of the control knob which in turn prevents overstretching or breaking of the traction wire. In yet another embodiment, for the control knob that rotates around the handle, there is a small protrusion on the handle that will hook with a small protrusion on the control knob. The control knob is free to rotate along the slideway within the range when the two protrusions does not meet but over-rotation of the control knob is prevented when the two protrusions hook up, thereby avoiding overstretching or breaking of the traction wire.

In one embodiment, the mapping-ablation catheter is rotatable in at least two modes. In one embodiment, the mapping-ablation catheter is rotatable after extending out of the guide catheter. In another embodiment, the mapping-ablation catheter is rotatable after fully retract into the guide catheter.

In one embodiment, the curvature of the steerable distal ends of the mapping-ablation catheter and guide catheter can be altered to adjust to the structure of the renal artery or the relative positions of abdominal aorta and renal artery so that the catheter can be more easily inserted into the renal artery and operated inside the renal artery.

In one embodiment, the curvature of the distal end of the guide catheter can be controlled with the control knob on the handle via the traction wire to ensure that the distal end of the guide catheter can enter the renal artery at a suitable angle.

In one embodiment, the distal end of the mapping-ablation catheter can form a certain curvature. In another embodiment, said curvature can ensure that the distal end of the catheter can maintain a given supportive force within the renal artery and also ensure that the distal end of the catheter can be anchored at a fixed position in the renal artery so that good contact between the distal end of catheter with the inner wall of the artery could be established and the ablation position is exactly the mapped position. In another embodiment, good contact between electrode and inner wall of the artery ensures that the electrical energy in electrical stimulations can be effectively delivered to the artery wall. In yet another embodiment, the energy in radio frequency ablations can be effectively delivered to the artery wall to ablate the nerve.

In one embodiment, to maintain the curvature of the distal end of the mapping-ablation catheter, Ni—Ti shape memory alloy material preformed to the desired shape is used so that the distal end can maintain the preformed curvature after assembled into the catheter. In another embodiment, the curvature is achieved by using traction wires, wherein one end of the traction wire is fixed to the distal end of the mapping-ablation catheter, and the other end is fixed to a stainless steel or Ni—Ti spring inside the handle. In one embodiment, when the mapping-ablation catheter is retracted within the guide catheter, the distal end is confined and stretches the traction wire while at the same time the spring is compressed. When the distal end of the mapping-ablation catheter is extended out of the guide catheter, its distal end is no longer confined and the spring restores naturally and pulls the traction wire to cause the bending of the distal end of the catheter.

In one embodiment, there is one or more electrodes at the tip of the mapping-ablation catheter. In one embodiment, said electrodes can deliver electrical energy for nerve mapping. In yet another embodiment, said electrodes can deliver radio frequency ablation energy for renal nerve ablation. In further embodiments, said electrodes can also release other types of energy for ablation, such as laser, or high intensity focused ultrasound, or used in other ablation techniques such as cryoablation, to deliver energy to renal arterial wall to remove renal sympathetic nerve or any other nerve.

In one embodiment, the tip of the mapping-ablation catheter provides one or more detecting devices. In one embodiment, said device is a temperature detecting device for users to measure the temperature in the artery or on the artery wall. In yet another embodiment, said device is a resistance detecting device for users to measure the resistance between the electrode and the artery wall to ensure good contact between the catheter tip and the artery wall.

In one embodiment, the catheter of this invention further provides a sealing mechanism to control fluid from entering or leaving the tip of the guide catheter. In one embodiment, said sealing mechanism is formed by the smooth surface of the electrode at the tip of mapping-ablation catheter fitting neatly on the smooth edge of the open end of the guide catheter. When the mapping-ablation catheter is retracted into the guide catheter, the close contact between the electrode mapping-ablation catheter and the edge of the open end of the guide catheter will prevent fluid from entering or leaving the open end of the guide catheter. When the sealing mechanism is opened, fluid can enter or leave the guide catheter as required by the user. In one embodiment, said fluid comprises contrast agents, blood or drugs. In one embodiment, the control of fluid to enter or leave the guide catheter is for injecting contrast agent for angiography, collecting blood sample from the renal artery or aorta, or injecting drugs into the renal artery or main artery.

In one embodiment, the end of the handle has a fluid-exchange conduit connected to the guide catheter wherein fluid can be led into the distal end of the guide catheter via said fluid-exchange conduit. In another embodiment, the distal end of the guide catheter further has one or more lateral holes for fluid to enter or leave the distal end of the guide catheter.

In one embodiment, the end of the handle has a connector for connecting to external instruments. In one embodiment, said external instrument is a controller for mapping and ablation wherein said controller provides the electrode of the mapping and ablating catheter with energy for stimulation or ablation of nerves.

In one embodiment, the choice of materials for the guide catheter depends on the hardness of the material which is selected based on the actual need required when placing the guide catheter into the renal artery. In one embodiment, said guide catheter is made of one or more polymeric materials of different hardness, wherein said materials comprises polyether block amide, polyimide or thermoplastic polyurethane. In one embodiment, said materials are distributed along different parts of the guide catheter based on their hardness: the material at the distal end is the softest, the materials in the middle part has an intermediate hardness and the material at the proximal end is the hardest. In another embodiment, the hardness of the materials is distributed in the range 90 A to 80 D in the Shore hardness scale. In a further embodiment, the different materials can be joined together directly by butt welding. The guide catheter has at least one big lumen and at least a small lumen. In one embodiment, said big lumen is for housing the mapping-ablation catheter. In another embodiment, the outer diameter of the guide catheter is from 1.0 to 5.00 mm, and the inner diameter is from 0.5 to 4.0 mm. In a further embodiment, said small cavity is designed to house the traction wire.

In one embodiment, the mapping-ablation catheter comprises a distal end and a proximal end, wherein said distal end and proximal end are made from pipes of woven reinforced polymeric material, said polymeric materials comprises polyether block amide, polyimide or thermoplastic polyurethane. In another embodiment, said proximal end is made from pipes of metallic materials, wherein said metallic materials comprises stainless steel or Ni—Ti alloy. In a further embodiment, the outer diameter of the mapping-ablation catheter is from 0.1 to 3.0 mm.

In one embodiment, the electrode at the tip of the mapping-ablation catheter is made of metallic materials, wherein said metallic materials comprises platinum, platinum-iridium alloy, gold or silver. In another embodiment, said electrode is circular, elliptical, spiral, spherical, cylindrical or annular in shape. In a further embodiment, the size of said electrode is suitable for use within the renal artery, and comprises a diameter of 0.1-4 mm or a length of 0.1-4 mm.

In one embodiment, the handle is made of polymeric materials comprising polyoxymethylene, acrylonitrile butadiene styrene, polycarbonate, polyamide or polymethylmethacrylate.

In one embodiment, the traction wire is made of materials such as stainless steel or Ni—Ti alloy.

In one embodiment, the catheters of this invention can be in different modes during mapping or ablation based on the actual need during operation. In one embodiment, the mapping-ablation catheter is fully retracted into the guide catheter when its tip is placed into the lumen of renal artery for mapping and ablation.

In one embodiment, the device of this invention is used in conjunction with all types of medical devices that is compatible with it, wherein said medical devices comprise catheter guide wire, traction guide wire, catheter sheath, dilator, or intervention devices for cardiovascular and renal vascular diseases. In one embodiment, said catheter guide wire can be placed into the blood vessel of a patient in advance so as to guide the distal end of the guide catheter to a desired position. In yet another embodiment, said traction guide wire aids in placing the distal end of the catheter to a suitable position.

This invention further provides a method of using the present catheter device for mapping the distribution of renal nerves so that the renal nerve distribution on the renal artery will be mapped and the ablation points in the renal artery can be identified in order to optimize the renal nerve ablation procedure. In one embodiment, the method comprises the following steps: placing the distal end of the catheter comprising the mapping-ablation catheter and the guide catheter into the renal artery lumen; manipulating the control knobs on the handle to move the distal end of the mapping-ablation catheter or guide catheter so that the electrode of the mapping-ablation catheter establishes good contact with the renal artery wall; delivering electrical stimulation to the renal artery via said electrode while monitoring one or more physiological parameters for any changes; analyzing the renal nerve mapping data comprising said physiological changes to provide information about renal nerve distribution and to effectively guide clinical physicians in the renal denervation procedure. In one embodiment, said physiological parameters comprise blood pressure, heart rate, heart rate variability, muscle sympathetic nerve activity or renal norepinephrine overflow level. In another embodiment, when electrical stimulation at a position results in changes in said physiological parameters, there is distribution of sympathetic nerve, and the stimulated position is suitable for ablation. In yet another embodiment, when the electrical stimulation at a position results in negative changes in said physiological parameters, there is distribution of parasympathetic nerve, and ablation should be avoided at the stimulated position.

In one embodiment, analysis of the renal nerve mapping data comprising the changes in the physiological parameters provide information about renal nerve distribution which can effectively guide clinical physicians in the renal denervation procedure.

This invention further provides method for mapping and ablating renal nerves with the devices described above and comprises the steps of:

(1) Placing the distal end of the device into the abdominal aorta via a puncture on femoral artery;
(2) Bend the distal end of the device to adjust to the structure of the renal artery and the relative position between the renal artery and abdominal aorta for easier entry into the renal artery;
(3) Extending the mapping-ablation catheter out of the guide catheter, and establish good contact between the electrode at the tip of the mapping-ablation catheter and the renal arterial wall;
(4) Delivering electrical energy to the position in contact with the electrode to stimulate any underlying nerves while the physiological response in heart rate, blood pressure and/or ECG are monitored concurrently. A stimulated position will be considered as a suitable location for ablation with underlying sympathetic nerve if the blood pressure, heart rate and/or heart rate variability derived from ECG are increased. Ablation should be avoided at a stimulated position considered to have underlying parasympathetic nerve if the blood pressure, heart rate and/or heart rate variability derived from ECG are decreased, or the heart rate alone decreases;

(5) Applying radio frequency energy to the identified ablation position via the electrode at the tip of the mapping-ablation catheter to ablate the nerve while the tip of the mapping-ablation catheter remains stationary;

(6) Monitoring the physiological response in heart rate, blood pressure and/or ECG during ablation; both blood pressure and heart rate will rise if the radio frequency energy has been successfully delivered to the sympathetic nerve.

(7) Delivering electrical energy again to the position in contact with the electrode to stimulate the underlying nerve after the ablation; the underlying nerve has been successfully ablated if both blood pressure and heart rate remain unchanged.

(8) Rotating the mapping-ablation catheter to bring the electrode at its tip to another position on the renal artery wall; and (9) Repeating steps (1)-(8) at the new contact position if necessary.

Further details on the nerve mapping procedure are disclosed in the published international applications PCT/IB2012/054303 filed on Aug. 24, 2012 and PCT/IB2012/054310 filed on Aug. 24, 2012.

EXAMPLE 1

FIGS. 1-1 to 1-4 show one of the embodiments of this invention. As shown in FIG. 1-1, the catheter comprises a steerable guide catheter (11) having lumens, a steerable mapping-ablation catheter (12) having a distal end with preformed shape housed inside the guide catheter, a handle (13) which contains the controlling components, a fluid-exchange conduit (14) connected to the guide catheter at the end of the handle, a connector (15) at the end of the handle for connecting to the mapping and ablating controller, and the traction wires that connect the tip of the guide catheter to the controlling components.

In one embodiment, the handle (13) and the controlling components contained within are made of polyoxymethylene, acrylonitrile butadiene styrene, or polymethylmethacrylate.

In one embodiment, the guide catheter (11) has an outer diameter of 2.66 mm, there is a small lumen of diameter 0.4 mm for the traction wire to pass through and a large lumen of 1.57 mm in diameter for the mapping-ablation catheter to pass through. The guide catheter (11) is made of 3 kinds of thermoplastic polyurethane each having different hardness; the distal end is the softest, the middle part has an intermediate hardness and the proximal end is hardest. In one embodiment, the hardness for these three parts are respectively 90 A to 40 D, 40 D to 70 D, and 70 D to 80 D on the Shore hardness scale. In one embodiment, the three types of materials are directly butt welded together.

In one embodiment, the mapping-ablation catheter (12) has an outer diameter of 1.1 mm; its distal end is made of woven polyimide, and its proximal end is made of stainless steel.

FIG. 2-1 shows the distal end of the mapping-ablation catheter in the same embodiment shown in FIG. 1-1. The curvature of the distal end of the mapping-ablation catheter is maintained by traction wires (24), wherein one end of the traction wire (24) is fixed to the distal end of mapping-ablation catheter (12), and the other end is fixed to a stainless steel or Ni—Ti alloy inside the handle (13). When the mapping-ablation catheter is retracted into the guide catheter, the distal end is confined and stretches the traction wire (24), while at the same time the spring is compressed. When the distal end of the mapping-ablation catheter (12) is extended out of the guide catheter (11), its distal end is no longer confined and the compressed spring restores naturally and pulls the traction wire (24) which causes bending of the distal end of the catheter. In one embodiment, the mapping-ablation catheter is provided with an electrode (22) and a temperature detecting device and resistance detecting device (23).

In one embodiment, the electrode (22) is a round electrode made from platinum-iridium alloy, having a diameter of 2.33 mm. The electrode can deliver both electrical and radio frequency energy.

FIG. 2-2 shows the sealing mechanism at the distal end of the same embodiment shown in FIG. 1-1. In one embodiment, the sealing mechanism between the tip of the mapping-ablation catheter (12) and guide catheter (11) is formed by the smooth surface of the round electrode (22) fitting neatly on the smooth edge of the open end of the guide catheter (11). The traction wire (24) of the mapping-ablation catheter and the traction wire (26) of the guide catheter are made of stainless steel or Ni—Ti alloy.

In one embodiment, the controlling components in the handle (13) comprise three control knobs (16, 17, 18), a sliding block (31), a structural component (33), a rotation-fixing block (34), gears or gear set (35) and a fixing block (36).

In one embodiment, the first control knob (16) drives the sliding block (31) with a screw thread mechanism, rotating the first control knob (16) makes the sliding block (31) moves linearly on the slideway (32). One end of a traction wire is fixed to the sliding block (31) while the other end is connected to the tip of the guide catheter (12). The distal end of the guide catheter (11) will be bent as the traction wire is pulled.

In one embodiment, the second control knob (17) contacts the rotation-fixing block (34) via the structural component (33), the rotation-fixing block (34) has a groove ring at the point of contact with the structural component (33) which ensure that the structural component will not rotate with the rotation-fixing block when the rotation-fixing block rotates. When the second control knob (17) is pushed, the control knob (17) drives the rotation-fixing block (34) to move forward and backward via the structural component (33). The electrode (22) at the tip of the catheter is fixed with respect to the rotation-fixing block (34) such that the electrode will move according to the movement of the rotation-fixing block. As a result, when the second control knob (17) is moved forward or backward, the mapping-ablation catheter (12) will extend out of or withdraw into the guide catheter (11). In one embodiment, calibrated markings on the second control knob (17) allow precise control of the length of the mapping-ablation catheter that is extended out of or retracted into the guide catheter so that the spacing between ablation points is, for example, at least 5 mm.

In one embodiment, the third control knob (18) contacts with the rotation-fixing block (34) via a gear set (35), the outside of the rotation-fixing block (34) is designed with teeth so that motion from the gears or gear set (35) could be transmitted. The mapping-ablation catheter (12) is fixed with respect to the rotation-fixing block (34) such that it moves according to the movement of the rotation fixing block (34). The fixing block (36) fixes the mapping-ablation catheter (12) by pressing against the proximal end of the catheter (e.g. stainless steel pipe) under the action of a screw. Rotating the third control knob (18) will transmit this motion to the gears or gear set (35) which then rotates the rotation-fixing block (34) such that the mapping-ablation catheter

(12) will rotate around the central axis of the open end of the guide catheter (11). In one embodiment, calibrated markings on the third control knob (18) ensure the mapping-ablation catheter can be precisely controlled to rotate by, for example, 15° each time.

The mapping-ablation catheter (12) in one embodiment can rotate under two modes. In the first mode, the distal end of the mapping-ablation catheter (12) is extended out of the guide catheter (11) when it is rotated; while, in the second mode, the distal end of the mapping-ablation catheter (12) is fully retracted into the guide catheter (11) when it is rotated.

EXAMPLE 2

In this example, the second control knob (17) and the third control knob (18) are the same control knob (19) (FIG. 3-1), that is, the same control knob (19) can control the mapping-ablation catheter to extend or withdraw and rotate; however, an interlock device ensures that rotation is not possible when this control knob is pushed or pulled. On the other hand, it is not possible to extend or withdraw the mapping-ablation catheter when this control knob is rotating. In one embodiment, moving a single control knob forward and backward can make the mapping-ablation catheter (12) extend out of or withdraw into the guide catheter (11) (FIG. 3-3); rotating the same single control knob (19) can make the mapping-ablation catheter (12) rotate around the central axis of the open end of the guide catheter (11) (FIG. 3-4).

Figures 1, 3:
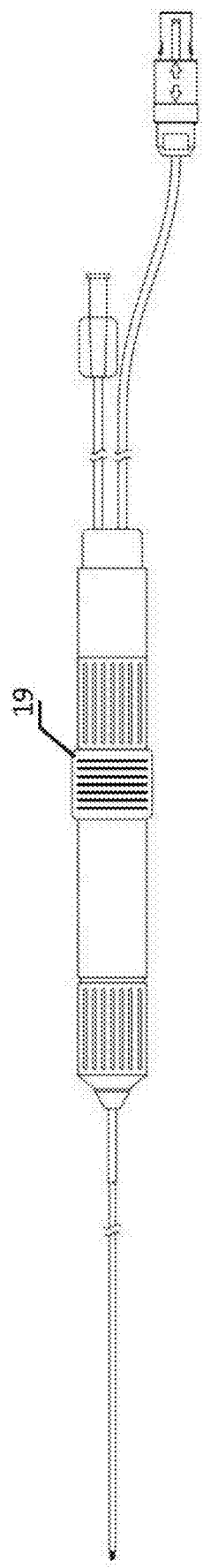
Figures 2, 3:
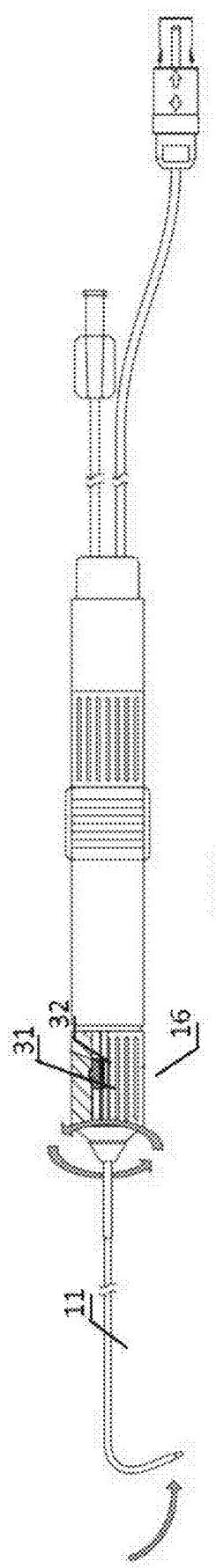
Figure 3:
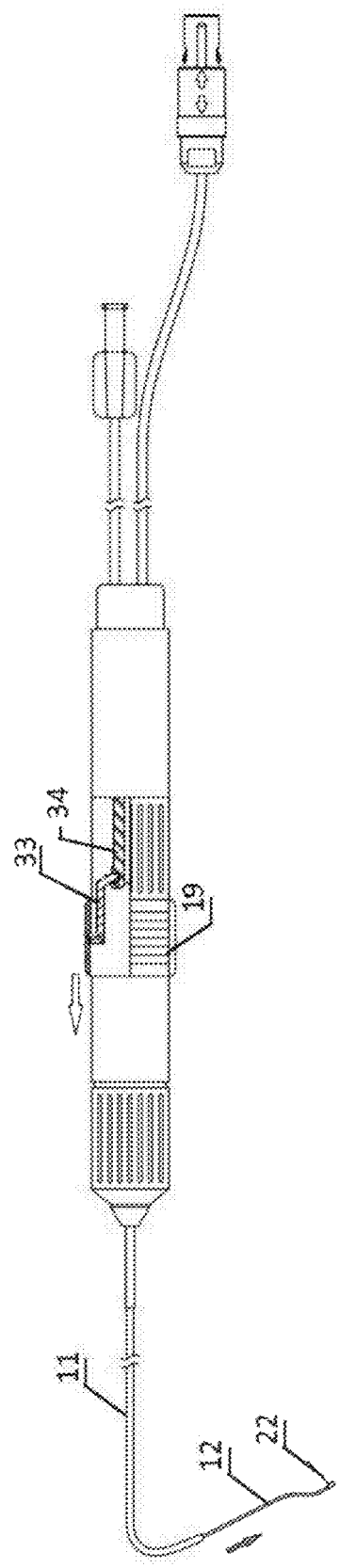
Figures 3, 4:
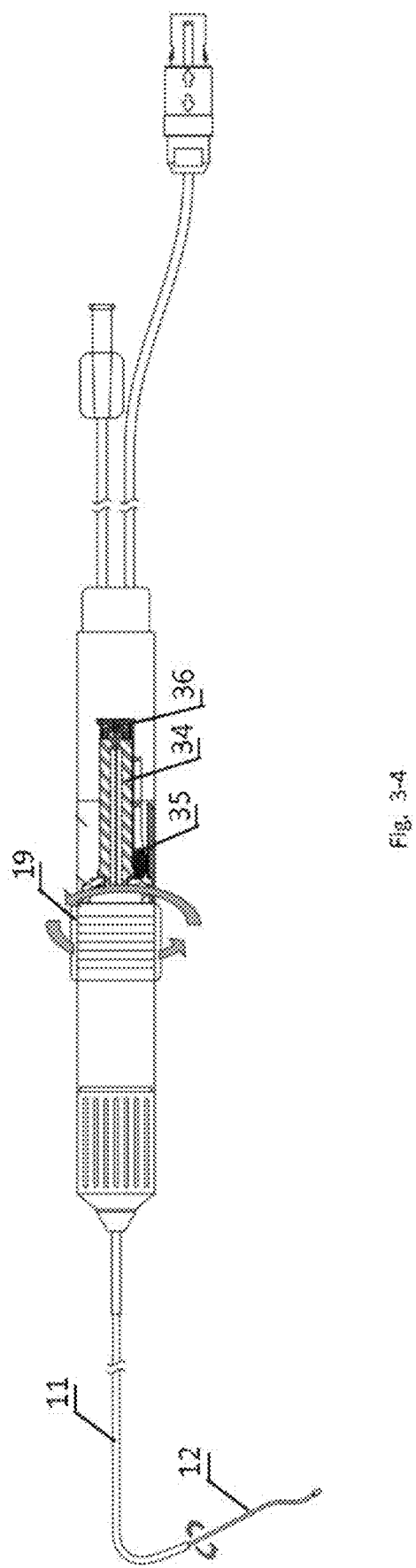

FIGS. 3-2 to 3-4 show the internal structure of the embodiment in example 2. The controlling components in the handle (13) comprise two control knobs (16, 19), a sliding block (31), a structural component (33), a rotation-fixing block (34), gears or gear set (35) and a fixing block (36).

In one embodiment, the first control knob (16) drives the sliding block (31) with a screw thread mechanism, rotating the first control knob (16) causes the sliding block (31) to move linearly on the slideway (32). Since one end of the traction wire is fixed to the sliding block (31) while the other end is connected to the tip of the guide catheter (12), the guide catheter (11) will be bent as the traction wire is pulled (FIG. 3-1).

In one embodiment, the second control knob (19) contacts the rotation-fixing block (34) via the structural component (33) and the rotation-fixing block (34) has a groove ring at the point of contact with the structural component (33) to ensure that the structural component will not rotate with the rotation fixing block when the rotation-fixing block rotates. When the second control knob (19) is pushed, the control knob (19) drives the rotation-fixing block (34) to move forward and backward via the structural component (33). The electrode (22) at the tip of the catheter is fixed with the rotation-fixing block (34) such that the electrode will move according to the movement of the rotation-fixing block. As a result, when the second control knob (19) is moved forward and backward, the mapping-ablation catheter (12) will extent out of or withdraw into the guide catheter (11). In one embodiment, calibrated markings on the second control knob (19) allow precise control of length of the mapping-ablation catheter that is extended out of or retracted into the guide catheter so that the spacing between ablation points can be made at intervals of at least, for example, 5 mm.

In one embodiment, the second control knob (19) contacts with the rotation-fixing block (34) via a gear set (35), the outside of the rotation-fixing block (34) is designed with teeth so that motion from the gears or gear set (35) could be transmitted. The mapping-ablation (12) is fixed with respect to the rotation-fixing block (34) such that it moves according to the movement of the rotation-fixing block (34). The fixing block (36) fixes the mapping-ablation catheter (12) by pressing against the proximal end of the catheter (e.g. stainless steel pipe) under the action of a screw. Rotating the second control knob (19) will transmit this motion to the gears or gear set (35) which then rotates the rotation-fixing block such that the mapping-ablation catheter (12) will rotate around the central axis of the open end of the guide catheter (11). In one embodiment, calibrated markings on the second control knob (19) ensure that rotations of the mapping-ablation catheter can be precisely made by, for example, 15° each time. This example is identical to the first example in all other aspects.

EXAMPLE 3

In this example, the curvature of the distal end of mapping-ablation catheter is maintained by using shape memory Ni—Ti alloy material with a preformed shape (25) so that the distal end can maintain the preformed curvature after assembled into the catheter. This example is identical to the first example in all other aspects.

EXAMPLE 4

In this example, the guide catheter (11) is made of three kinds of thermoplastic polyurethane of different hardness; the distal end is the softest, the middle part has an intermediate hardness while the proximal end is the hardest. In one embodiment, the hardness for these three parts are respectively 90 A to 40 D, 40 D to 70 D, and 70 D to 80 D on the Shore hardness scale. In one embodiment, the three types of materials are directly butt welded together. This example is identical to the first example in all other aspects.

EXAMPLE 5

In this example, the detecting device at the head of the mapping-ablation catheter (12) is a resistance detecting device. This example is identical to the first example in all other aspects.

EXAMPLE 6

In this example, there is both a resistance detecting device and a temperature detecting device (23) at the tip of the mapping-ablation catheter (12). This example is identical to the first example in all other aspects.

EXAMPLE 7

In one embodiment, when any of the devices described above is used, the connector (15) is connected with an external mapping and ablating controller to provide the electrode at the head of mapping-ablation catheter with the electrical energy required to stimulate nerves and the radio frequency energy required to ablate nerves.

In one embodiment, a method for mapping and ablating renal nerved with any of the devices described above comprises:
(1) Placing the distal end of the catheter into the abdominal aorta via a puncture on femoral artery;
(2) Bend the distal end of the device by rotating the first control knob (16) to adjust to the structure of the renal artery and the relative position between the renal artery and abdominal aorta for easier enter the renal artery;

(3) Extending the mapping-ablation catheter (12) out of the guide catheter (11) by pushing the second control knob (17 or 19), and establish good contact between the electrode (22) at the tip of the mapping-ablation catheter and the renal arterial wall;

(4) Delivering electrical energy to the position in contact with the electrode (22) to stimulate any underlying nerves while the physiological response in heart rate, blood pressure and/or ECG are monitored concurrently. A stimulated position will be considered a suitable location for ablation with underlying sympathetic nerve if the blood pressure, heart rate and/or heart rate variability derived from ECG are increased. Ablation should be avoided at a stimulated position considered to have underlying parasympathetic nerve if the blood pressure, heart rate and/or heart rate variability derived from ECG are decreased, or the heart rate alone decreases;

(5) Applying radio frequency energy to the identified ablation position via the electrode (22) at the tip of the mapping-ablation catheter to ablate the nerve while the tip of the mapping-ablation catheter (12) remains stationary;

(6) Monitoring the physiological response in heart rate, blood pressure and/or ECG during ablation; both blood pressure and heart rate will rise if the ratio frequency energy has been successfully delivered to the sympathetic nerve;

(7) Delivering electrical energy again to the position in contact with the electrode (22) to stimulate the underlying nerve after the ablation. The underlying nerve has been successfully ablated if both blood pressure and heart rate remain unchanged;

(8) Rotating the third control knob (18) or the second control knob (19) to rotate the mapping-ablation catheter (12) to bring the electrode (22) at its tip to another position on the renal artery wall, and repeat steps (1)-(8) at the new contact position if necessary.

REFERENCES

1. Brandt M C, Mahfoud F, Reda S et al. Renal sympathetic denervation reduces left ventricular hypertrophy and improves cardiac function in patients with resistant hypertension. JACC. 2012, 59: 901-909.
2. Brinkmann J, Heusser K, Schmidt B M et al. Catheter-Based Renal Nerve Ablation and Centrally Generated Sympathetic Activity in Difficult-to-Control Hypertensive Patients: Prospective Case Series. Hypertension. 2012; 60:1485-1490
3. Chinushi M, Izumi D, Iijima K et al. Blood Pressure and Autonomic Responses to Electrical Stimulation of the Renal Arterial Nerves Before and After Ablation of the Renal Artery. Hypertension. 2013(61):450-456.
4. D'Agrosa L S. Cardiac arrhythmias of sympathetic origin in the dog. Am. J. Physiol. Heart Circ. Physiol. 1977, 233(5): H535-H540.
5. Dasgupta I, Watkin R, Freedman J et al. Renal sympathetic denervation for resistant hypertension in a patient with severe CKD: a first report. J. Hum. Hypertens. 2012, 26(10): 639.
6. Esler M D, Krum H, Sobotka, P A et al. Renal sympathetic denervation in patients with treatment-resistant hypertension (the Simplicity HTN-2 Trail): a randomised controlled trial. Lancet. 2010, 376: 1903-1909.
7. Esler M. The autonomic nervous system and cardiac arrhythmias. Clin. Auton. Res. 1992, 2(2):133-135.
8. Hering D, Mahfoud F, Walton A S et al. Renal Denervation in moderate to severe CKD. JASN. 2012, 23(7): 1250-1257.
9. Hering D, Walton A S, Krum H, et al. Renal sympathetic nerve ablation in moderate to severe chronic renal failure: a short term safety and efficacy pilot study. Hypertension. 2012, 60(2): 502.
10. Krum H, Schlaich M, Whitbourn R et al. Catheter-based renal sympathetic denervation for resistant hypertension: a multicentre safety and proof-of-principle cohort study. Lancet. 2009, 373: 1275-1281.
11. Mahfoud F, Schlaich M, Kindermann I et al. Effect of renal sympathetic denervation on glucose metabolism in patients with resistant hypertension: a pilot study. Circulation. 2011, 123: 1940-1946.
12. Sadowski J; Bartus K; Kapelak B et al. Catheter-based renal sympathetic denervation for resistant hypertension: durability of blood pressure reduction out to 24 months. Hypertension. 2011, 57: 911-917.
13. Schlaich M P, Socratous F, Hennebry S et al. Sympathetic activation in chronic renal failure. JASN. 2009, 20(5): 933-939.
14. Sobotka P A, Krum H, Bohm M et al. The role of renal denervation in the treatment of heart failure. Curr. Cardiol. Rep. 2012, 14(3): 285-292.
15. Witkowski A, Prejbisz A, Florczak E et al. Effects of renal sympathetic denervation on blood pressure, sleep apnea course, and glycemic control in patients with resistant hypertension and sleep apnea. Hypertension. 2011, 58: 559-565.

What is claimed is:

1. A device for mapping and ablating the renal nerves distributed on the renal artery, comprising a guide catheter, a mapping-ablation catheter, a handle and a connector, wherein
said guide catheter has at least one lumen and a distal end with adjustable curvature;
said mapping-ablation catheter is housed in the at least one lumen of the guide catheter and has a distal end that comprises one or more electrodes and one or more detecting devices, said distal end of the mapping-ablation catheter is curved and can be extended out of or retracted into the guide catheter and is rotatable along the central axis of the open end of the guide catheter;
said handle connects the guide catheter and mapping-ablation catheter and comprises one or more controlling components, said controlling components are for controlling the movement of the guide catheter and mapping-ablation catheter; said handle further comprises an interlock, said interlock prevents said mapping-ablation catheter from: i) rotating when extending or retracting into said guide catheter; ii) extending or retracting into said guide catheter when said one or more controlling components are controlling said mapping-ablation catheter to rotate around the central axis of the open end of the guide catheter; and
said connector is designed to supply energy to the one or more electrodes.

2. The device of claim 1, wherein said handle further comprises a fluid-exchange conduit connected to the guide catheter for controlling fluid entering or leaving the guide catheter.

3. The device of claim 1, wherein said detecting devices comprise temperature detecting device and resistance detecting device.

4. The device of claim 1, wherein a sealing mechanism is formed between the mapping-ablation catheter and guide catheter to control fluid entry or exit.

5. The device of claim 1, wherein said electrodes comprise the one or more electrodes for delivering electrical energy, radio frequency energy, laser energy, high intensity focused ultrasound, or for carrying out cryoablation.

6. The device of claim 1, wherein the material at the distal end of said guide catheter is the softest, the material at the middle part of the guide catheter has an intermediate hardness and the material at the proximal end of the guide catheter is the hardest with the hardness of the materials distributed in the range 90 A to 80 D in the Shore hardness scale.

7. The device of claim 1, wherein the curvature of the distal end of said mapping-ablation catheter is maintained:
   by using a traction wire, one end of the traction wire is fixed to the distal end of the mapping-ablation catheter while the other end is fixed to a spring inside the handle, wherein when the distal end of the mapping-ablation catheter is retracted into the guide catheter, the distal end is confined and stretches the traction wire to compress the spring, wherein when the distal end of the mapping-ablation catheter is extended out of the guide catheter, its distal end is no longer confined and the spring restores naturally and pulls the traction wire to cause the bending of the distal end of the catheter; or
   by using Ni-Ti shape memory alloy with a preformed shape so that the distal end can maintain the preformed curvature after assembled into the catheter.

8. The device of claim 1, wherein said controlling components comprise a control knob that causes the distal end of the guide catheter to bend.

9. The device of claim 1, wherein said controlling components comprise a control knob that causes the distal end of the mapping-ablation catheter to extend out of or withdraw into the guide catheter.

10. The device of claim 1, wherein said controlling components comprise a control knob that causes the distal end of the mapping-ablation catheter to rotate.

11. The device of claim 1, wherein said controlling components comprise a control knob that causes the distal end of the mapping-ablation to extend out of or withdraw into the guide catheter, and causes the distal end of the mapping-ablation catheter to rotate.

12. A method of using the device of claim 1 for mapping and ablating the renal nerves distributed on a renal artery, said method comprising the following steps:
   (i) inserting the distal end of the guide catheter of the device into renal artery via the abdominal aorta;
   (ii) extending the mapping-ablation catheter out of the guide catheter to establish good contact between the electrode and the renal artery wall; and
   (iii) providing energy to the electrode, so that said energy is delivered to the renal artery wall.

13. The method of claim 12, wherein the curvature of the distal end of the guide catheter is adjustable to make it easier to enter the renal artery.

14. The method of claim 12, wherein the length of the mapping-ablation catheter extending out of the guide catheter is controllable to allow selection of a position to establish good contact between the electrode and the renal artery wall.

15. The method of claim 12, wherein said mapping-ablation catheter can be controlled to rotate around the central axis of the open end of the guide catheter to allow selection of a position to establish good contact between the electrode and the renal artery wall.

16. The method of claim 12, wherein said energy to be delivered into the renal artery wall comprises energy for nerve stimulation and energy for nerve ablation.

17. The method of claim 16, wherein said energy comprises electric energy, radio frequency energy, laser energy, high density focusing supersonic wave, or for cryoablation.

18. The method of claim 12, further comprising the step of moving the guide catheter or mapping-ablation catheter, after step (iii), to establish good contact between the electrode and the renal artery wall at a new location.

* * * * *